United States Patent
Scatizzi

(10) Patent No.: US 9,255,246 B2
(45) Date of Patent: Feb. 9, 2016

(54) USE OF LACTOBACILLI INHIBITING GAS PRODUCING COLIFORM BACTERIAL ISOLATED FROM INFANTS AFFECTED BY COLIC

(75) Inventor: Gianna Scatizzi, Novara (IT)

(73) Assignee: Probiotical S.p.A., Novara (IT)

( * ) Notice: Subject to any disclaimer, the term of this patent is extended or adjusted under 35 U.S.C. 154(b) by 0 days.

(21) Appl. No.: 13/806,936

(22) PCT Filed: Jun. 28, 2010

(86) PCT No.: PCT/IB2010/001554
§ 371 (c)(1),
(2), (4) Date: Apr. 17, 2013

(87) PCT Pub. No.: WO2012/001440
PCT Pub. Date: Jan. 5, 2012

(65) Prior Publication Data
US 2013/0195823 A1    Aug. 1, 2013

(51) Int. Cl.
*A61K 35/747* (2015.01)
*C12R 1/225* (2006.01)
*C12R 1/25* (2006.01)
*A23L 1/30* (2006.01)
*C12N 1/20* (2006.01)

(52) U.S. Cl.
CPC ............... *C12N 1/20* (2013.01); *A61K 35/747* (2013.01); *C12R 1/225* (2013.01); *C12R 1/25* (2013.01)

(58) Field of Classification Search
None
See application file for complete search history.

(56) References Cited

U.S. PATENT DOCUMENTS

2004/0161422 A1    8/2004  Ranganathan
2004/0185032 A1*   9/2004  Burrell ..................... 424/93.45

FOREIGN PATENT DOCUMENTS

| RU | 2391393 C1 | 6/2010 |
| WO | WO-03/071883 A1 | 9/2003 |
| WO | WO 2004028460 A2 * | 4/2004 |

OTHER PUBLICATIONS

The Olive Oil Source/Useful Number Conversions. Datasheet [online]. The Olive Oil Source, Copyright 1998-2013 [retrieved on Sep. 26, 2013]. Retrieved from the Internet: <URL: http://www.oliveoilsource.com/page/useful-number-conversions>. p. 2.*

Metcalf TJ, et al., Simethicone in the Treatment of Infant Colic: "A Randonmized, Placebo-Controlled, Multicenter Trial.", Pediatrics, 94(1): pp. 29-34, 1994.

Sferra TJ et al., "Gastrointestinal gas formation and infantile colic.", Pediatr Clin North Am., 43(2): pp. 489-510, 1996.

* cited by examiner

*Primary Examiner* — John S Brusca
*Assistant Examiner* — Sharon M Papciak
(74) *Attorney, Agent, or Firm* — McCarter & English, LLP; Danielle L. Herritt; Jill Ann Mello

(57) ABSTRACT

The present invention relates to a composition comprising two probiotic strains of bacteria capable of performing an antioxidant and/or antibacterial and competitive action against species of coliform bacteria that produce gas by fermentation of sugar, in particular lactose, isolated from infants affected by colic.

16 Claims, 1 Drawing Sheet

Figure no. 1

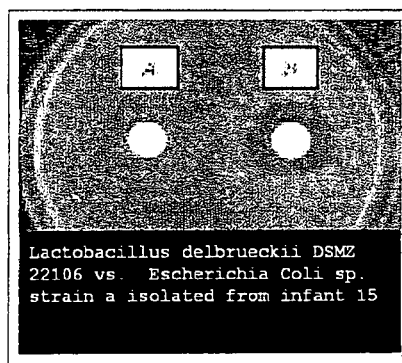

Figure no. 1:
disc A = impregnated with supernatant;
disc B = impregnated with a suspension comprising from $1 \times 10^4$ to $1 \times 10^6$ whole cells.

Lactobacillus delbrueckii DSMZ 22106 vs. Escherichia Coli sp. strain a isolated from infant 15

Figure no. 2

Figure 2:
disc A = impregnated with supernatant;
disc B = impregnated with a suspension comprising from $1 \times 10^4$ to $1 \times 10^6$ whole cells.

Lactobacillus delbrueckii DSMZ 22106 vs. Klebsiella pneumoniae sp. strain a isolated from infant 12

USE OF LACTOBACILLI INHIBITING GAS PRODUCING COLIFORM BACTERIAL ISOLATED FROM INFANTS AFFECTED BY COLIC

RELATED APPLICATIONS

This application is a 35 U.S.C. §371 national stage filing of International Application No. PCT/IB2010/001554, filed Jun. 28, 2010. The entire contents of this application is explicitly incorporated herein by reference.

The present invention relates to a strain of probiotic bacteria capable of inhibiting gas producing coliform bacteria isolated from infants affected by colic. Furthermore, the present invention relates to a food composition or supplement or pharmaceutical composition comprising said strain of bacteria for use in preventive and/or curative treatments of intestinal disorders and for colic in infants/babies.

It is well known that infantile colic represents one of the most frequent disorders in the first three months of life of an infant. It is likewise known that the etiology of infantile colic is not yet completely clear and is likely to be multifactorial.

In the past few years, there has been an increase in data pointing to an involvement of intestinal bacterial flora in the pathogenesis of colic. Recent experimental studies seem to suggest that an alteration of the microbial environment of babies affected by colic could cause a dysregulation of intestinal motor function and an increase in the production of gas, which, by resulting in excessive flatulence, represents one of the classic symptoms of the disorder.

Finally, it is known that infants affected by colic are more frequently colonised by *Clostridium difficile*, a gas producing microorganism, compared to healthy infants.

At present, simethicone seems to be the most indicated treatment for colic. Simethicone is recommended in the treatment of colic, even though there exist studies which tend to disprove its real effectiveness in vivo versus placebo in babies with colic (Metcalf T J, et al. Simethicone in the Treatment of Infant Colic: A Randomized, Placebo-Controlled, Multi-center Trial. 1994, *Pediatrics*. 94(1): 29-34; Sferra T J, et al. Gastrointestinal gas formation and infantile colic. 1996, *Pediatr Clin North Am*. 43(2): 489-510).

Thus there remains a need to have a preventive and/or curative treatment for gastrointestinal disorders and colic in infants which is effective, free of side effects and easy to apply.

The Applicant undertook to resolve the problem related to the preventive and/or curative treatment for gastrointestinal disorders in infants/babies. In particular, the Applicant addressed the problem related to the preventive and/or curative treatment for colic in infants/babies.

Following intense research activity, the Applicant selected specific probiotic strains of bacteria belonging to the species *Lactobacillus delbrueckii*.

All the strains have been deposited in accordance with the Treaty of Budapest and are accessible to the public on request from the competent Depositing Authority. Such Depositing Authorities include DSMZ (Deutsche Sammlung von Mikroorganismen und Zellkulturen GmbH) Inhoffenstr. 7B, D-38124 Braunschweig, Germany.

The object of the present invention is a probiotic strain of bacteria selected from the group comprising the strains of bacteria belonging to the species *Lactobacillus delbrueckii*.

BRIEF DESCRIPTION OF THE DRAWINGS

FIG. 1 shows the results of an experiment demonstrating inhibition of growth of a strain of *E. coli* around a disc that had been impregnated with a suspension of cells of *Lactobacillus delbruekii* MB386 DSM 22106.

FIG. 2 shows the results of an experiment demonstrating inhibition of growth of a strain of *K. pneumoniae* around a disc that had been impregnated with a suspension of cells of *Lactobacillus delbruekii* MB386 DSM22106.

DETAILED DESCRIPTION

Preferred embodiments of the present invention are set forth below in the following detailed description, without in any way limiting the scope of the present invention.

Table no. 1 refers to the antagonistic activity shown on plates by *Lactobacillus delbrueckii* MB386 DSM 22106 vs. the coliforms isolated from infants with colic. The inhibition of the growth of pathogens is expressed as the radius of the inhibition halo that develops around the discs impregnated with whole cells of the selected *lactobacillus*.

Table no. 2 refers to the quantification of total coliforms in the faecal samples of 20 infants affected by colic during manifestation of the disorder.

(*) the total number of coliforms was determined by counting the colonies that had grown on MacConkey agar plates, whereas the species concentrations were determined using the species-specific PCR-fingerprinting method and by ribotyping.

The selected probiotic strains of bacteria act as inhibitors of the proliferation of coliform bacteria. Preferably, said coliform bacteria are selected from the group comprising the coliform bacteria that produce gas by fermentation of sugar, preferably lactose.

The selected probiotic strains of bacteria have a proven antibacterial and/or antimicrobial activity (inhibiting activity) against the species of *Escherichia coli, Klebsiella pneumoniae, Klebsiella oxytoca, Enterobacter aerogenes, Enterobacter cloacae* and, finally, *Enterococcus faecalis* isolated from infants affected by colic and belonging to the genus of coliform bacteria involved in the fermentation of lactose and production of intestinal gas, the latter being considered a major concomitant cause in the disorder of infantile colic.

In particular, said coliform bacteria are selected from the group comprising the bacteria *Escherichia coli*.

In a preferred embodiment, the probiotic strain of bacteria is *Lactobacillus delbrueckii* MB386, deposited with the DSMZ (Deutsche Sammlung von Mikroorganismen and Zellkulturen GmbH; Inhoffenstr. 7B, D-38124 Braunschweig, Germany) by the company Steve Jones Srl, Florence, Italy, on 10 Dec. 2008 and having the filing number DSM 22106.

The strain *Lactobacillus delbrueckii* MB386 DSM 22106 has an effective antibacterial and/or antimicrobial activity against the coliform bacteria isolated from infants affected by colic.

A further object of the present invention is a food composition or supplement comprising at least one probiotic strain of bacteria belonging to the species *Lactobacillus delbrueckii*, as specified above.

A further object of the present invention is a composition comprising at least one probiotic strain of bacteria belonging to the species *Lactobacillus delbrueckii*, as specified above, for use as a medication.

All the above-mentioned compositions of the present invention have application in the preventive and/or curative treatment of disorders or pathologies connected to diarrhoea, colic, indigestion and gastric hyperacidity, irritable bowel syndrome, flatulence, peptic ulcer, stomach or duodenal ulcer, dyspepsia, Crohn's disease, abdominal lesions and biliary diseases.

In a preferred embodiment, all of the above-mentioned compositions of the present invention have application for use in the preventive and/or curative treatment of subjects affected by gastrointestinal disorders, colic and flatulence, in particular in infants/babies.

In a preferred embodiment, all of the above-mentioned compositions of the present invention further comprise at least one other strain of bacteria having antioxidant properties, selected from the group comprising the strains of bacteria belonging to the species *Lactobacillus plantarum*; preferably said strain is *Lactobacillus plantarum* LP1, deposited with the DSMZ (Deutsche Sammlung von Mikroorganismen and Zellkulturen GmbH; Inhoffenstr. 7B, D-38124 Braunschweig, Germany) by the company Steve Jones Srl, Florence, Italy, on 10 Dec. 2008 and having the filing number DSM 22107.

The strain *Lactobacillus plantarum* LP1 DSMZ 22107 has antioxidant properties. The strain *Lactobacillus plantarum* LP1 DSMZ 22107 is a probiotic strain, as it shows an antioxidant activity associated with excellent vitality, tested in vitro, in gastric juice and bile, which implies a tolerance to intestinal transit.

All of the above-described compositions are effective in preventing bacterial infections and curbing gastrointestinal symptoms and disorders, colic and flatulence.

In one embodiment of the present invention, the food composition or supplement or pharmaceutical composition may contain the above-mentioned bacterial strains of the present invention in microencapsulated form, i.e. coated with a composition containing at least one lipid (lipid composition), preferably of vegetable origin.

Alternatively, the food composition or supplement or pharmaceutical composition may comprise the above-mentioned bacterial strains of the present invention as microencapsulated bacteria and non-microencapsulated bacteria.

Said lipid composition comprises at least one lipid, and said at least one lipid is of vegetable origin.

Advantageously, said lipid of vegetable origin is selected from the group comprising saturated fats.

Advantageously, saturated fats are used having a melting point lower than 75° C., preferably comprised from 45° C. to 65° C.

In a preferred embodiment, said saturated fats are selected from the group comprising mono- and di-glycerides of saturated fatty acids, polyglycerols esterified with saturated fatty acids, and free saturated fatty acids. Preferably said saturated fats are selected from among polyglyceryl distearate, glyceryl palmitostearate and hydrogenated vegetable fats of non-lauric origin.

In a first embodiment, the above-mentioned bacterial strains of the present invention are mono-coated.

Practically speaking, a single coating with a single lipid is realized. Advantageously, the single coating is based on polyglyceryl distearate (commercial name Plurol Stearique WL 1009).

The above-mentioned mono-coated strains of bacteria of the present invention are placed in the food composition or supplement or pharmaceutical composition of the present invention.

In a second embodiment, the above-mentioned strains of bacteria of the present invention are double-coated.

Practically speaking, a double coating is realized, in succession, with two lipids different from each other.

Advantageously, the two lipids selected are a hydrogenated palm fat (Tm=60° C.) and a glycerol dipalmitostearate (Tm=57-60° C.); they are sprayed onto the lyophilate in succession. a double covering is applied to the lyophilate: the first with the hydrogenated palm fat (for example with Revel C) and the second with the glycerol dipalmitostearate (for example Precirol Ato 5) in a ratio by weight of 3:1 to each other, advantageously 2:1, for example ⅔ by weight of the first and ⅓ by weight of the second. The aforesaid species of bacteria are present in a quantity comprised from 0.1% to 75% by weight, preferably from 0.5% to 15% by weight; even more preferably from 1% to 10% by weight, relative to the total weight of the composition or supplement. However, said percentage relative to the total weight of the composition depends on the product type of the composition or supplement.

In a preferred embodiment, the composition or supplement contains coated and/or uncoated bacteria in a concentration comprised from $1 \times 10^6$ to $1 \times 10^{11}$ CFU/g, preferably from $1 \times 10^8$ to $1 \times 10^{10}$ CFU/g.

In a preferred embodiment, the composition or supplement contains bacteria in a concentration comprised from $1 \times 10^6$ to $1 \times 10^{11}$ CFU/dose, preferably from $1 \times 10^8$ to $1 \times 10^{10}$ CFU/dose. The dose may be comprised from 0.2 g to 10 g; for example it may be 0.25 g, 1 g, 3 g, 5 g or 7 g.

The probiotic bacteria used in the present invention can be in solid form, in particular in the form of a powder, dehydrated, sprayed or lyophilized powder. The bacteria can be coated and/or uncoated. The bacteria, preferably in microencapsulated form (coated), can be microencapsulated using ordinary techniques well known to those skilled in the art and employing machinery that is known and available in the pharmaceutical industry. For example, a fluid bed technique may be used (e.g. top spray or bottom spray), in which coating materials of a lipid nature are used.

During microencapsulation, thermal control of the production process is important. In particular, it is important to control the temperature of the lipid used in order to avoid the mortality of the strains used.

In a preferred embodiment, the composition or supplement is in the form of an oily suspension comprising:
  at least one food oil selected from the group comprising: olive oil, maize oil, soybean oil, linseed oil, peanut oil, sesame oil, fish oil and rice oil, said at least one oil being present in a quantity greater than or equal to 70% by weight, relative to the total weight of the suspension, and
  at least one probiotic strain of bacteria selected from the group comprising the strains of bacteria belonging to the species *L. delbrueckii* and *L. plantarum*, said strain being present in a quantity less than or equal to 30% by weight, relative to the total weight of the suspension.

In a preferred embodiment, the oil of the suspension is only olive oil; preferably it is olive oil in a mixture with maize oil and/or soybean oil and/or linseed oil.

In a preferred embodiment, the oily suspension can also comprise, in a quantity comprised from 0.1 to 15% by weight, relative to the total weight of the suspension, at least one finely subdivided food compound selected from the group comprising silica, silicon dioxide, silica gel, colloidal silica, precipitated silica, talc, magnesium silicate, magnesium oxide, magnesium carbonate, calcium silicate, lecithin, mono- or di-glycerides such as glyceryl monostearate, glyceryl monooleate, Plurol Oleique acid, starch, modified starches, konjac gum, xanthan gum, gellan gum and carrageenan.

In a preferred embodiment, the oily suspension can also comprise, in quantity comprised from 0.5 to 25% by weight, relative to the total weight of the suspension, at least one prebiotic fibre and/or bifidogenic carbohydrate selected from among inulin, fructo-oligosaccharides (FOS), galacto- and transgalacto-oligosaccharides (GOS and TOS), gluco-oligosaccharides (GOSα), xylo-oligosaccharides (XOS), chitosan oligosaccharides (COS), soy oligosaccharides (SOS), isomalto-oligosaccharides (IMOS), maltodextrin, resistant starch, pectin, psyllium, arabinogalactans, glucomannans, galactomannans, xylanes, lactosaccharose, lactulose, lactitol, acacia fibre, carruba fibre, oat fibre, bamboo fibre and citrus fibre.

In a preferred embodiment, the oily suspension comprises at least one fibre and at least one carbohydrate selected from among gluco-oligosaccharides (GOSα), fructo-oligosaccharides (FOS), inulin and/or maltodextrin.

In a preferred embodiment, the oily suspension comprises *Lactobacillus delbruekii* MB386 DSM 22106 and *Lactobacillus plantarum* LP1 DSMZ 22107 coated (microencapsulated) with a single coating (or with two coatings) with at least one lipid having a melting point below 75° C., preferably comprised from 45 to 65° C., as stated above.

The oily suspension of the present invention is prepared according to techniques well known to those skilled in the art and using known machinery.

Practically speaking, a given quantity of oil is introduced into a container provided with stirring and heating means. Subsequently the probiotic bacteria in solid form are gradually added under stirring so as to avoid the formation of lumps and agglomerations. Once the addition of bacteria has ended, the oily substance is maintained under stirring for a time comprised from 1 to 30 minutes, if necessary with slight heating to a temperature comprised from 24 to 40° C., preferably from 30 to 35° C.

In a preferred embodiment of the present invention, the probiotic bacteria can be used in microencapsulated form, i.e. coated with a composition containing at least one lipid, preferably of vegetable origin. The microencapsulated bacteria are then added to the oil using the same operating methods as described above.

In another embodiment of the present invention, the bacteria added to the oil can be in the form of microencapsulated bacteria and "naked", non-microencapsulated bacteria.

The bacteria, preferably in microencapsulated form, can be microencapsulated using the ordinary techniques known to those skilled in the art. For example, a fluid bed technique may be used (e.g. top spray or bottom spray), in which coating materials of a lipid nature are used.

In a preferred embodiment, saturated vegetable fats are used having a melting point below 75° C., preferably comprised from 45 to 65° C.

In a preferred embodiment, saturated vegetable fats having a certain degree of hydrophilicity can be used; these can be selected from among mono- and di-glycerides of saturated fatty acids, polyglycerols esterified with saturated fatty acids, and free saturated fatty acids.

For example, it is possible to use polyglyceryl distearate (commercial name Plurol Stearique WL 1009), glyceryl palmitostearate (commercial name Precirol Ato 5), saturated fatty acids (commercial name Revel C) or hydrogenated vegetable fats of non-lauric origin.

In a preferred embodiment, the ratio by weight between lyophilized microorganism and the lipid coating material which coats it is 50:50 or 40:60.

In a first embodiment, two lipids, a hydrogenated palm fat (Tm=60° C.) and a glycerol dipalmitostearate (Tm=57-60° C.) are sprayed onto the lyophilate in succession, i.e. a double covering is applied to the lyophilate: the first with the hydrogenated palm fat and the second with the glycerol dipalmitostearate in a ratio of 3:1 to each other. A double coating of the cells ensures better sealing of the bacteria from the environment, producing a continuous film without pores communicating with the outside. However, this wrapper must open at the intestinal level to release the bacteria and allow them to colonise. The lipids selected are in fact resistant to acid pH's, so that the coating remains intact in the stomach, but sensitive to even slightly basic pH's, so as to allow the formation of holes in the coating during its passage through the intestine.

The oily suspension contains the bacteria in a quantity less than or equal to 30% by weight, comprised from 0.5 to 20% by weight, relative to the total weight of the suspension; preferably in a quantity comprised from 0.5 to 10%; even more preferably in a quantity comprised from 1.5 to 5% by weight, relative to the total weight of the suspension.

The oily suspension has valid application for use as a medication for the treatment of intestinal disorders, such as colic in paediatric subjects.

A study was conducted to evaluate the role of gas producing coliform bacteria in the etiology of infantile colic.

Practically speaking, a randomised prospective study was conducted in which 49 infants affected by infantile colic and 35 healthy infants were recruited; they were aged between 20 and 90 days, corresponding to the gestational age, exclusively breastfed and free of diseases of the gastroenteric system. Faecal samples were collected from both groups of infants at pre-established times and examined within the next 48 hours. The study had the aim of establishing whether there existed significant qualitative/quantitative differences in the two groups of infants with respect to the presence of gas producing coliforms.

Typical genera included in the group of coliforms are: *Citrobacter, Enterobacter, Escherichia coli, Klebsiella* and other minor groups. The identification of the most representative species isolated from the faecal samples was carried out at a molecular level using PCR (Polymerase Chain Reaction) and automated ribotyping techniques. Finally, the ability of the microbial colonies to produce gas by fermentation of lactose and other sugars was examined.

The molecular and phenotypic identification of the various species of coliforms showed a different colonisation pattern in the two groups, with and without colic, and in particular the concentration of the species *Escherichia coli* showed to be significantly higher in the group of infants with colic [(6.04 $Log_{10}$ versus 4.47 $Log_{10}$) $CFUg^{-1}$ of faeces]. It is believed that precisely the anomalous concentration of this species of *Escherichia coli* may contribute to the development of the disorder.

It cannot be ruled out that the abundance of coliform species observed in our study in the infants affected by the pathology may be associated with a decrease in some other species, not yet identified, of bacteria beneficial for the host, resulting in possible consequences on the host's state of health.

Experimental Part

1. Introduction

The Applicant conducted a study aimed at selecting probiotic strains of bacteria belonging to the genus *Lactobacillus*, selected and evaluated in relation to the effectiveness of its antioxidant, antibacterial and antimicrobial action against species of coliform bacteria isolated from infants affected by colic.

Tens of strains of coliform bacteria, producers of gas by fermentation of sugar, particularly lactose, were isolated from the faeces of infants affected by colic in order to evaluate in vitro the inhibition of their growth by the probiotic strains of bacteria belonging to the genus *Lactobacillus* which were taken into consideration.

2. Isolation of Strains and Culture Conditions

For the purpose of quantifying and examining the presence of coliforms, faecal samples were collected from 49 exclusively breastfed infants affected by colic, which had manifested itself 6±1 days prior to enrolment. The isolation of strains was carried out on selective plates of MacConkey Agar (DIFCO n. 0075.17.1), which is the medium generally used to isolate and quantify enteric bacteria (called "coliforms") after placing them in ideal conditions for growth: 37° C. in a controlled atmosphere.

After 12 hours of incubation the colonies that appear on the plate are counted and all the morphological differences among the colonies themselves are carefully observed. The numerical results are shown as $Log_{10}$ of colony forming units (CFU) per gram of faeces. Each isolated colony is then taken individually and inoculated in a tube of LB (Luria-Bertani) liquid medium to obtain pure cultures.

3. Identification of Colonies of Coliforms

A total of 20 faecal cultures obtained from faeces of infants affected by colic were analyzed for the purpose of isolating the most representative genera of coliforms.

Species-specific recognition of the colonies was achieved using two different molecular identification procedures: primer-specific PCR and automated ribotyping. Combining the results obtained by both methods made it possible both to identify the isolated strains with a high degree of accuracy and define which species are the most representative of the population of coliforms that colonises the intestines of infants affected by colic.

Finally, each bacterial species was quantified by calculating in what percentage it represented the entire isolated population of coliforms.

a. Automated Ribotyping

Automated strain-specific ribotyping involves the use of an extremely sophisticated instrument: RiboPrinter Microbial Characterization System (Qualicon Inc., Wilmington, Del., USA). The bacterial colonies isolated on the plate are taken individually; after a thermal step and through the use of lytic enzymes there is obtained the release of DNA, which is cleaved by the restriction endonuclease EcoR1. Finally, the DNA fragments, separated by gel electrophoresis, are analyzed using the modified Southern blotting technique. The hybridization analysis is translated into an image of separate chemiluminescent bands which the instrument transforms into electronic data, or a Riboprinter pattern, which it captures and stores in memory. The final identification is achieved by comparing the Riboprinter pattern obtained with the ones stored in the Dupont database of the instrument. The profiles with a similarity at least equal to 93%, as calculated by means of an appropriate algorithm, are combined to form a dynamic Ribogroup which reflects the relations or genetic identities among the isolated colonies.

b. Primer-Specific PCR

For the purpose of the molecular identification of the coliform bacteria, ribosomal DNA fragments of the 16S-23S internal transcribed spacer regions were amplified.

The pure colonies isolated on the plate were individually picked and re-suspended in sterile distilled water and then lysed for 5 min at 95° C. so as to allow the release of DNA. The amplification reactions were obtained using the universal primers: 16S—for (5'-GCTGGATCACCTCCTTTC-3') and 23S-rev (5'-AGTGCCAAGGCATCCACC-3').

The amplification reactions were carried out in a Biometra TGradient Thermal Cycler (Biometra, Gottingen, Germany), setting a specific thermocycling program. The amplificates were separated by gel electrophoresis; the fragments of approximately 400 bp were purified using a QIAquick Gel Extraction Kit (QIAGEN, Hilden, Germany); finally, the DNA fragments amplified with the 16S and 23S primers were submitted to automated sequence analysis.

4. Gas Production by Coliform Bacteria

The ability to produce gas mediated by all the isolated coliform bacteria was evaluated by inoculating each individual strain in a liquid LB broth and/or Lauryl sulphate tryptose (LST) broth containing 10 g/L of lactose as the sole carbon source. 24-48 hours following the inoculation and after incubation at 35° C., the bacterial cultures were examined for the presence of gas bubbles in the liquid medium according to the method of Jiang T et al.[51]. The presence of gas indicated a positive reaction to the test.

5. Random Selection of Lactic Bacteria and Culture Conditions

The strains of lactic bacteria whose antimicrobial activity vs. the coliform bacteria of infants was tested were 30 randomly selected strains representative of different species of lactic bacteria. The lactobacilli used in this study came from the ATCC and DSMZ collections (American Type Culture Collection, Rockville, Md., and Deutsche Sammlung von Mikroorganismem and Zellkulturen, Braunschweig, Germany, respectively).

The taxonomy of the strain of *Lactobacillus plantarum* LP1 DSM 22107 was confirmed at the species level by automated ribotyping. The strain selected by screening, *Lactobacillus delbrueckii* MB386, comes from the German DSMZ collection (DSM 20074 or ATCC 9649).

All of the lactobacilli used in the study in question were cultivated for 24 hours at 37° C. in Lactobacilli MRS broth—Difco Laboratories, Sparks, Md., USA-(MRS) containing 0.5 g/L of cysteine as the reducing agent.

6. Assay to Evaluate Antimicrobial Properties

The antimicrobial properties were evaluated using two strategies: inhibition of bacterial growth on plates, or the Kirby-Bauer disc diffusion method (1940), and preparation of co-cultures of the selected lactic bacteria with one or more coliform bacteria originating from infants affected by colic.

a) Antimicrobial Activity on Plates

The purpose of this method is to examine the inhibiting effect of the strains of lactobacilli considered on the in vitro growth of coliform bacteria isolated from infants. The strains of lactobacilli were made to grow in an anaerobic culture in MRS liquid medium for 48 hours at 37° C. The cells, collected from the culture by centrifugation, were re-suspended in saline solution until obtaining a concentration of $10^4$ and $10^6$ cells/ml, as determined by measuring the optical density at 600 nm. The supernatant, separated from the biomass, was neutralized to pH 7.0. The cellular suspension containing the coliform bacteria considered in a concentration of $10^3$ and $10^6$ cells/ml was distributed over a solid medium of LB (Luria Bertani) agar (0.7%); subsequently, two discs (6 mm in diameter) were placed on the medium, one impregnated with the cellular suspension of the *lactobacillus* considered and the other with the associated supernatant. The control was prepared in the same manner, but by placing two non-impregnated sterile discs on the medium.

After 18 hours' incubation at 37° C., the inhibition area of the pseudopathogen which appeared around the discs was measured.

b) Antimicrobial Activity in Liquid Co-Cultures

The antagonism exerted by the lactobacilli considered in the present study against the growth of coliform bacteria was confirmed by co-incubating, in a liquid medium, each potential probiotic inhibitor with the most representative coliforms isolated from the infants. The inoculum of the co-culture was obtained by separately cultivating the probiotic and coliforms in optimal conditions. The bacterial cells from each of the two cultures were collected by centrifugation and re-suspended in a fresh equivalent medium to avoid any conditioning of growth that might occur in co-culture due to unwanted variations in pH or to a reduction in nutrilites. A liquid medium of modified LB broth (Luria Bertani with the addition of 3% yeast extract, pH 7) was inoculated with a total of $10^5$ CFU/ml of lactobacilli and the same concentration of a known bacterial suspension of coliforms. The control was prepared in the same manner, replacing the probiotic inoculum with the fresh medium alone, without any cells.

The co-cultures and controls thus prepared were incubated at 37° C. in controlled microaerophilia and after 8-10 hours the antagonistic activity performed by the probiotics was evaluated by determining the inhibition of growth of the coliform bacteria. This was calculated by subtracting the number of coliform bacteria found in the co-incubation tube from the number of coliform bacteria from the control tube, inoculated with coliform bacteria only. The CFU/ml of the vital bacterial population that had grown was measured by distributing known aliquots of the co-cultures and controls on media selective both for lactobacilli (Lactobacilli MRS agar) and coliforms (MacConkey agar) (Annuk 2003); finally, the change in pH after 24 hours of co-incubation was determined. The results as regards the bacterial concentrations of lactobacilli and coliforms were expressed in $Log_{10}$ CFU/ml.

The examples that follow are provided for illustrative purposes and are not intended to limit the scope of the invention in any way.

Example 1

The selected strain *Lactobacillus* delbruekii MB386 DSM 22106 was cultured anaerobically in a liquid medium for 48 hours at 37° C. An overnight culture of the coliform bacteria *Escherichia coli* sp. strain a isolated from infant 15 (see table no. 2), who presented with clinically diagnosed symptoms of infantile colic, was treated as in the previously described assay for analyzing the antimicrobial activity on plates. A suspension having a concentration of $10^3$-$10^6$ cells/ml of coliform bacteria was distributed over solid LB medium; subsequently, two discs were placed on the medium, one (disc B, FIG. 1) impregnated with the suspension of collected cells of *Lactobacillus* delbruekii MB386 DSM 22106 and the other with the respective neutralized supernatant (disc A, FIG. 1).

The plate thus prepared was allowed to rest at 4° C. for at least one hour. After 18 hours' incubation at 37° C., a measurement was made of the area of inhibition of growth of the *Escherichia coli* sp. strain a that had developed around the two discs.

Result: a halo of inhibition of growth of the examined *Escherichia coli* strain isolated from infant 15 affected by infantile colic was visible only around the disc that had been impregnated with the suspension of cells of *Lactobacillus delbruekii* MB386 DSM 22106, whereas no inhibition area appeared around the disc impregnated with the corresponding supernatant of the *lactobacillus*. The halo of inhibition of growth of the coliform bacteria was measured and showed to have a radius of 13 mm (FIG. 1).

Example 2

An evaluation was made of the antimicrobial activity manifested by the probiotic *lactobacillus Lactobacillus delbruekii* MB386 DSM 22106 vs. *Klebsiella pneumoniae* strain b isolated from infant 12 affected by infantile colic (table no. 2). For the purposes of the test, the two bacterial strains were treated as described in example 1.

Result: a measurement was made of the area of inhibition of growth of the *Klebsiella pneumoniae* strain b, isolated from infant 12 with infantile colic, which appeared around the disc that had been impregnated with the suspension of cells of *Lactobacillus delbruekii* MB386 DSM 22106. In this case as well, no antagonistic activity resulted from the disc impregnated only with the supernatant devoid of cells originating from the culture of the *lactobacillus*. The inhibition halo was measured to have a radius of 12.5 mm, as may be seen from FIG. 2.

Example 3

An evaluation was made of the antimicrobial activity manifested by the probiotic *lactobacillus Lactobacillus delbrueckii* MB386 DSM 22106 vs. all the strains of *Escherichia coli, Klebsiella pneumoniae, Klebsiella oxytoca, Enterobacter aerogenes, Enterobacter cloacae* and, finally, *Enterococcus faecalis* isolated from the infants affected by infantile colic and from the healthy controls.

For the purposes of the test, the probiotic strain of lactic bacteria and the coliform bacteria isolated from the infants were treated as described in example 1.

Result: in general, the examined strain of *Lactobacillus delbrueckii* MB386 DSM 22106 always showed an inhibiting activity against all of the coliforms tested. A control plate was prepared by placing on the LB agar medium two analogous sterile discs impregnated neither with the cell suspension nor with the culture broth alone. The control never showed any inhibitory effect on the growth of the coliform strains examined. All the results obtained from the tests performed to evaluate the antagonistic activity manifested on plates by the *lactobacillus* considered and expressed as the mean radius of the inhibition areas are reported in table no. 1.

Example 4

An evaluation was also made of the antimicrobial activity manifested by the selected probiotic *lactobacillus Lactobacillus plantarum* LP1 DSM 22107 vs. all the strains of *Escherichia coli, Klebsiella pneumoniae, Klebsiella oxytoca, Enterobacter aerogenes, Enterobacter cloacae* and, finally, *Enterococcus faecalis* isolated from the infants affected by infantile colic and from the healthy controls. For the purposes of the test, the probiotic strain of lactic bacteria and the coliform bacteria isolated from the infants were treated as described in example 1.

Result: in general, the examined strain of *Lactobacillus plantarum* LP1 DSM 22107 never showed any inhibitory effects on the coliforms examined.

Example 5

An evaluation was made of the antimicrobial activity manifested together by the two probiotic strains of lactic bacteria of the invention, *Lactobacillus delbruekii* MB386 DSM 22106 and *Lactobacillus plantarum* LP1 DSM 22107, vs. all the isolated strains of coliform bacteria: *Escherichia coli, Klebsiella pneumoniae, Klebsiella oxytoca, Enterobacter aerogenes, Enterobacter cloacae* and, finally, *Enterococcus faecalis* isolated from the infants affected by infantile colic. For the purposes of the test, the two probiotic strains of lactic bacteria were cultivated separately as described in example 1 and, similarly, each coliform bacterium was treated as described in example 1. A suspension having a concentration of $10^3$-$10^6$ cells/ml of coliform bacterium was distributed over solid LB medium. Subsequently, two discs were placed on the medium, one impregnated with a suspension of collected cells of *Lactobacillus delbruekii* MB386 DSM 22106 of known concentration plus a suspension having an analogous concentration of cells collected from the culture of *L. plantarum* DSM 22107, and the other with a mixture formed from the two neutralized supernatants, devoid of cells, originating from the cultures of the two lactic bacteria. The plate thus prepared was allowed to rest at 4° C. for at least one hour. After 18 hours' incubation at 37° C., a measurement was made of the area of inhibition of growth of the coliform considered which had developed around the two discs, where present.

Results: the tests on antibacterial activity performed in synergy revealed that the area of inhibition of the growth of each coliform strain isolated from infants with colic always appeared only around the disc that had been impregnated with the two suspensions of cells of *L. delbruekii* DSM 22106 and *L. plantarum* DSM 22107, whereas no inhibition halo appeared around the disc impregnated with the respective supernatants, originating from the cultures of the two lactic bacteria. Finally, the inhibition halo originating from the whole cells was measured and showed to have a mean radius comparable to that resulting from the sole antagonistic activity manifested by *L. delbruekii* DSM 22106 (table no. 1).

Example 6

The antagonistic activity of *Lactobacillus delbruekii* MB386 DSM 22106 in vitro was evaluated by inoculating a modified LB medium, already described in the paragraph regarding the method of evaluating the antimicrobial activity in liquid co-culture, with a total of $10^5$ CFU/ml of lactobacilli and an equal concentration of cells of *Escherichia coli* strain a, isolated from infant 15 affected by colic (table no. 3). A second tube containing modified LB was inoculated only with cells of coliform bacteria. The co-culture and control were incubated at 37° C. in microaerophilia and after 8-hours the antagonistic activity manifested by the lactic bacteria against the *Escherichia coli* strain was evaluated.

In order to measure the growth of *Lactobacillus* delbruekii MB386 DSM 22106 and the *Escherichia coli* strain resulting both from the co-incubation tests and from the control, the CFU/ml of the two bacterial strains were evaluated both at the time 0 of inoculation and at 24 hours by distributing aliquots of broth from the co-culture and from the control over both MRS agar containing 0.2% vancomycin (selective for lactic bacteria) and MacConkey agar (selective for *Escherichia coli*); finally the change in pH in the co-incubated tube and in the control after 24 h was determined.

Results: at t0 (time of inoculation) $2.7 \times 10^5$ cells of *Lactobacillus* delbruekii DSM 22106 were co-inoculated with $5.0*10^5$ cells of *Escherichia coli*. The initial pH was 6.8. After 24 hours (t24), the count on selective plates revealed $7.0 \times 10^9$ CFU/ml of *Lactobacillus* delbruekii DSM 22106 and $5.0*10^5$ CFU/ml of *Escherichia coli*, while the pH had decreased to 4.3. In the control tube only $4.5 \times 10^5$ CFU/ml of *Escherichia coli* were inoculated at t0; the inoculum of lactic bacteria was replaced by adding an equal volume of fresh medium alone, without any cells. After 24 hours of incubation, the count revealed $1.0 \times 10^9$ CFU/ml of inoculated *Escherichia coli*. The pH of the medium, equal to 6.8, remained unchanged after 24 hours.

Example 7

Like in example 5, but an evaluation was made of the antimicrobial activity expressed by a combination of the two strains of *Lactobacillus* delbruekii MB386 DSM 22106 and *Lactobacillus plantarum* LP1 DSM 22107 when co-incubated with the coliform strains most representative of each identified species isolated from the infants.

The antagonistic activity performed in "synergy" by the two lactic bacteria was evaluated by inoculating the modified LB medium with a total of $10^2$ CFU/ml of *L. delbruekii* DSMZ 22106 and $10^2$ cells of *L. plantarum* DSMZ 22107 and, finally, an equal concentration ($10^4$) of cells of the coliform bacteria considered. A second tube containing modified LB was inoculated only with the cells of both lactic bacteria. The co-culture and control thus prepared were incubated at 37° C. in microaerophilia and after 8-10 hours the resulting antagonistic activity, if any, was evaluated.

In order to measure the growth of the lactic bacteria and coliforms resulting both from the co-incubation tests and from the control, the CFU/ml of each bacterium was evaluated both at the time 0 of inoculation and after 24 hours, as described in example 5.

The total CFU/ml of lactic bacteria was calculated together with the CFU/ml of the coliform considered; finally, the change in pH in the co-incubated tube and in the control after 24 hours was determined.

Results: irrespective of the species and of the infant from whom they were isolated, the concentration of coliform bacteria in co-culture with the two probiotic lactobacilli was reduced by at least 4 decimal logarithmic units (from $E10^9$ to $E10^5$) compared to the control tube. The pH, always measured before and after the 24 hours of incubation, varied by a value of at least 3.3±0.4 when the tubes were co-incubated with both lactic bacteria and the strain of coliform bacteria, whereas the pH in the control tubes always remained unchanged.

From the foregoing it emerges that the strain of *L. delbruekii* MB386 DSM 22106 has a clear antibacterial activity vs. the species *Escherichia coli, Klebsiella pneumoniae, Klebsiella oxytoca, Enterobacter aerogenes, Enterobacter cloacae* and, finally, *Enterococcus faecalis* isolated from infants affected by colic and belonging to the genus of coliform bacteria involved in the fermentation of lactose and production of intestinal gas, considered a major concomitant cause in the disorder of infantile colic.

Reducing the concentration of intestinal coliform bacteria is considered essential in order to maintain a stable equilibrium in the human intestinal microbiota, thus benefiting man's state of health.

TABLE NO. 1

Antagonistic activity shown by *Lactobacillus delbruekii* DSMZ 22106 on plates and expressed as the mean radius of the inhibition area

| isolated coliform bacteria | inhibition halo (mean radius of the area ± SD) |
| --- | --- |
| *Escherichia coli* | 10.23 ± 1.29 |
| *Klebsiella pneumoniae* | 9.83 ± 1.04 |
| *Klebsiella oxytoca* | 9.75 ± 1.06 |
| *Enterobacter aerogenes* | 10.25 ± 0.35 |
| *Enterobacter cloacae* | 10.25 ± 0.35 |
| *Enterococcus faecalis* | 10.16 ± 0.76 |

TABLE NO. 2

| Subjects no. | Total coliforms (CFU $g_{-1}$ faeces)* | No. of colonies morphologically different on plate | Dilution factor on plate | Species identified |
|---|---|---|---|---|
| 2 | $5.0 \times 10^6$ | 2 | a. $10^{-6}$<br>b. $10^{-6}$ | a. *E. coli*<br>b. *E. coli* |
| 3 | $1.0 \times 10^6$ | 2 | a. $10^{-6}$<br>b. $10^{-4}$ | a. *K. pneumoniae*<br>b. *E. coli* |
| 4 | $1.0 \times 10^7$ | 2 | a. $10^{-6}$<br>b. $10^{-6}$ | a. *E. coli*<br>b. *K. oxytoca* |
| 6 | $3.0 \times 10^8$ | 2 | a. $10^{-8}$<br>b. $10^{-7}$ | a. *E. coli*<br>b. *E. coli* |
| 7 | $2.0 \times 10^7$ | 1 | a. $10^{-7}$ | a. *E. faecalis* |
| 9 | $7.0 \times 10^3$ | 1 | a. $10^{-3}$ | a. *E. coli* |
| 12 | $4.0 \times 10^7$ | 2 | a. $10^{-7}$<br>b. $10^{-7}$ | a. *E. coli*<br>b. *K. pneumoniae* |
| 13 | $3.7 \times 10^7$ | 2 | a. $10^{-7}$<br>b. $10^{-5}$ | a. *E. coli*<br>b. *E. coli* |
| 15 | $3.4 \times 10^8$ | 2 | a. $10^{-6}$<br>b. $10^{-5}$ | a. *E. coli*<br>b. *E. coli* |
| 16 | $4.3 \times 10^8$ | 2 | a. $10^{-8}$<br>b. $10^{-5}$ | a. *E. coli*<br>b. *K. oxytoca* |
| 17 | $1.1 \times 10^6$ | 2 | a. $10^{-6}$<br>b. $10^{-5}$ | a. *E. coli*<br>b. *Enterobacter cloacae* |
| 18 | $8.1 \times 10^6$ | 2 | a. $10^{-6}$<br>b. $10^{-5}$ | a. *K. oxytoca*<br>b. *E. faecalis* |
| 22 | $1.1 \times 10^3$ | 1 | a. $10^{-3}$ | a. *E. coli* |
| 23 | $9.5 \times 10^6$ | 4 | a. $10^{-6}$<br>b. $10^{-6}$<br>c. $10^{-6}$<br>d. $10^{-5}$ | a. *K. oxytoca*<br>b. *E. aerogenes*<br>a. *E. coli*<br>b. *E. coli* |
| 24 | $1.0 \times 10^3$ | 1 | a. $10^{-3}$ | a. *E. coli* |
| 29 | $5.8 \times 10^8$ | 2 | a. $10^{-8}$<br>b. $10^{-7}$ | a. *E. coli*<br>b. *E. coli* |
| 32 | $2.7 \times 10^6$ | 4 | a. $10^{-6}$<br>b. $10^{-5}$<br>c. $10^{-5}$<br>d. $10^{-5}$ | a. *E. coli*<br>b. *K. oxytoca*<br>c. *K. pneumoniae*<br>d. *K. oxytoca* |
| 36 | $1.0 \times 10^4$ | 1 | a. $10^{-4}$ | a. *K. oxytoca* |
| 39 | $1.0 \times 10^4$ | 1 | a. $10^{-4}$ | a. *K. pneumoniae* |
| 48 | $2.6 \times 10^6$ | 1 | a. $10^{-6}$ | a. *K. oxytoca* |

*the total number of coliforms was determined by counting the colonies that had grown on MacConkey agar plates, whereas the species concentrations were determined using the species-specific PCR fingerprinting method and by ribotyping.

The invention claimed is:

1. A method of treating colic in a subject suffering from colic, the method comprising administering to said subject an effective amount of a food composition, a supplement or a pharmaceutical composition comprising the bacterial strain *Lactobacillus delbruekii* MB386, deposited with the DSMZ on Dec. 10, 2008 and having the filing number DSM 22106, thereby treating said colic in said subject suffering from colic.

2. The method of claim 1, wherein the food composition, or supplement, or pharmaceutical composition further comprises at least one other strain of bacteria having antioxidant properties.

3. The method of claim 2, wherein the strain of bacteria having antioxidant properties is *Lactobacillus plantarum* LP1, deposited with the DSMZ on Dec. 10, 2008 and having the filing number DSM 22107.

4. The method of claim 3, wherein said *Lactobacillus delbruekii* MB386 and said *Lactobacillus plantarum* LP1 are coated with a composition containing at least one lipid.

5. The method of claim 3, wherein the bacterial strains *Lactobacillus delbruekii* MB386 and *Lactobacillus plantarum* LP1 are coated with a first and second coating, wherein said first coating is a hydrogenated palm fat having a melting point of around 60° C., and wherein the second coating is a glycerol dipalmitostearate fat having a melting point from 57 to 60° C.

6. The method of claim 4, wherein the lipid is selected from the group comprising saturated fats having a melting point below 75° C.

7. The method of claim 6, wherein the melting point is from 45 to 65° C.

8. The method of claim 6, wherein the saturated fats are selected from mono- and di-glycerides of saturated fatty acids, polyglycerols esterified with saturated fatty acids, and free saturated fatty acids.

9. The method of claim 8, wherein the saturated fats are selected from polyglyceryl distearate, glyceryl palmitostearate, saturated fatty acids or hydrogenated vegetable fats of non-lauric origin.

10. The method of claim 1, wherein the food composition, or supplement, or pharmaceutical composition is in the form of an oily suspension comprising:
   at least one food oil selected from the group consisting of olive oil, maize oil, soybean oil, linseed oil, peanut oil, sesame oil, fish oil and rice oil, wherein
      said at least one oil is present in a quantity greater than or equal to 70% by weight, relative to the total weight of the suspension, and
   wherein the food composition, or supplement, or pharmaceutical composition further comprises a bacterial strain belonging to the species *L. plantarum*,
      wherein said bacterial strain *Lactobacillus delbruekii* MB386 or said bacterial strain belonging to the species *Lactobacillus plantarum* is present in a quantity less than or equal to 30% by weight, relative to the total weight of the suspension.

11. The method according to claim 10, wherein the oil of the suspension is olive oil.

12. The method of claim 11, wherein the olive oil is in a mixture with another oil selected from the group consisting of maize oil, soybean oil and linseed oil.

13. The method of claim 1, wherein the subject is an infant.

14. The method of claim 1, wherein said bacterial strain *Lactobacillus delbruekii* MB386 is an isolated bacterial strain.

15. The method of claim 1, wherein said food composition, said supplement or said pharmaceutical composition is administered orally.

16. The method of claim 1, wherein said bacterial strain *Lactobacillus delbruekii* MB386 is present in said food composition, said supplement or said pharmaceutical composition in the amount of $10^6$ to $10^{11}$ CFU/dose.

* * * * *

UNITED STATES PATENT AND TRADEMARK OFFICE
CERTIFICATE OF CORRECTION

| | |
|---|---|
| PATENT NO. | : 9,255,246 B2 |
| APPLICATION NO. | : 13/806936 |
| DATED | : February 9, 2016 |
| INVENTOR(S) | : Gianna Scatizzi |

It is certified that error appears in the above-identified patent and that said Letters Patent is hereby corrected as shown below:

In the Title on page 1 item (54)

Replace "BACTERIAL" WITH --BACTERIA--

Signed and Sealed this
Twenty-sixth Day of July, 2016

Michelle K. Lee
*Director of the United States Patent and Trademark Office*